United States Patent [19]

Taffe et al.

[11] Patent Number: 4,900,681

[45] Date of Patent: Feb. 13, 1990

[54] HYDRAZINE DETECTION

[76] Inventors: Patricia A. Taffe, 8085 Steeple Chase Ct., Springfield, Va. 22153; Susan L. Rose-Pehrsson, 3808 Stonebridge Rd., Alexandria, Va. 22306

[21] Appl. No.: 201,767

[22] Filed: Jun. 2, 1988

[51] Int. Cl.$^4$ .......................................... G01N 21/78
[52] U.S. Cl. .................... 436/106; 436/112; 436/164; 436/169; 436/902
[58] Field of Search ............... 436/106, 112, 128, 131, 436/164, 169, 902

[56] References Cited

U.S. PATENT DOCUMENTS

| | | | |
|---|---|---|---|
| 2,162,978 | 6/1939 | Seaton | 422/56 X |
| 2,206,282 | 7/1940 | Jacobius | 422/56 X |
| 3,455,656 | 7/1969 | Roberts et al. | 436/106 X |
| 4,271,121 | 6/1981 | Diller et al. | 436/902 X |
| 4,775,633 | 10/1988 | Rounbehler | 436/106 |
| 4,780,282 | 10/1988 | Holtzclaw et al. | 436/106 X |

FOREIGN PATENT DOCUMENTS

1254362  8/1986  U.S.S.R. ................. 46/169

OTHER PUBLICATIONS

Grdinic et al., Pharmazie, vol. 41, pp. 715–716, 1986.
Franc et al., Chemical Abstracts, vol. 106, Abstract No. 106:12065v, 1/12/87.
Blanxart et al., Chemical Abstracts, vol. 95, Abstract No. 95:231460c, 1981.
Maslii et al., Chemical Abstracts, vol. 98, Abstract No. 98:1188765, 1983.
Rychkova et al., Chemical Abstracts, vol. 101, Abstract No. 101:59864s, 1984.
Chernaya et al., Chemical Abtracts, vol. 103, Abstract No. 103:42284w, 1985.
The Merck Index, Tenth Edition, Edited by Windholz et al., Published by Merck & Co., Inc., Rahway, N.J., 1983, pp. 97 & 1419.
Shouquan, Chemical Abstracts, vol. 107, Abstract No. 107:12524q, 7/13/87.
Somova, Chemical Abstracts, vol. 85, Abstract No. 85:103332u, 1976.
Bakal et al., Chemical Abstracts, vol. 89, Abstract No. 89:16104k, 1978.

*Primary Examiner*—Robert J. Hill
*Attorney, Agent, or Firm*—Herbert L. Bello

[57] ABSTRACT

A solution of various benzaldehyde derivatives dissolved in suitable solvents are used in impinger sampling or as a coating on substrates to provide passive, real-time visual colorimetric indication of the presence of hydrazine and its derivatives.

15 Claims, 1 Drawing Sheet

HYDRAZINE DETECTION

This invention was made with Government support under NRL Contract No. N00014-86-C-2266. The Government has certain rights in this invention.

BACKGROUND OF THE INVENTION

1. Field of the Invention:

The present invention relates to the detection of hydrazine compounds and, more particularly, is directed toward real-time, passive detection of hydrazine compounds using benzaldehyde and its derivatives.

2. Description of the Prior Art:

Hydrazine is an extremely toxic chemical which is used in industry as a blowing agent for blow molded plastic products, for the synthesis of agricultural products, as a oxygen scavenger agent for water treatment to inhibit corrosion, pharmaceutical applications and as a rocket propellant. Due to the high toxicity of hydrazine, employers must meet specified standards for monitoring exposure levels of hydrazine for all employees who might be exposed. Currently, hydrazine monitoring is accomplished by use of expensive instrumentation which is transported to various facilities for non-continuous monitoring of air and water. Such instrumentation requires calibration regularly and is not particularly adapted for individual monitoring. A citric acid dosimeter collects analyte data, but not in real-time. The use of para -N, N-dimethylaminobenzaldehyde is a known wet chemical method, but it is not used as a dosimeter.

U.S. Pat. No. 3,455,656 discloses colorimetric detection of hydrazine compounds by means of a solid carrier that is impregnated with solutions containing a silicic acid and a molybdic acid. These methods have not been demonstrated for real-time, passive detection.

There are few commercial real-time detectors or acceptable techniques available for detection of hydrazine exposure at threshold limiting values (100-500 parts-per-billion, depending upon the specific hydrazine to be detected). Passive electrochemical techniques have not proven reliable; liquid sorbent badges lack the required precision and accuracy; strong acids on supports are not applicable to monomethylhydrazine; and collection on citric acid coated disks does not provide real-time analysis.

A need exists for a simple, inexpensive and reliable method and device which provides a passive, real-time visual indication of hydrazine exposure as well as individual personnel monitoring of exposure to hydrazine.

SUMMARY OF THE INVENTION

It is an object of the present invention to provide a simple, inexpensive and reliable method and device for passive detection of hydrazine and its derivatives.

It is another object of the present invention to provide a method and device to provide a real-time colorimetric indication of exposure to hydrazine and its derivatives.

It is yet another object of the invention to provide a colorimetric dosimeter for real-time detection of threshold limiting values of hydrazine and monomethylhydrazine in air. The invention involves the condensation of an aromatic aldehyde with a hydrazine to form a colored hydrazone. The aldehyde indicators are characterized by a para substituent which activates the chromophore.

It is a further object of the present invention to provide a method and device which provides a real-time colorimetric indication of the presence of threshold limiting values of hydrazine and its derivatives. The invention is characterized by the use of various benzaldehyde derivatives that are dissolved in suitable solvents, typically methanol or isopropanol, to provide a solution which is used as a collection media in impinger sampling of low levels of hydrazine in air and as a coating on substrates to provide an indication of exposure to hydrazine and its derivatives. In a second application, solvents such as diethylether or acetone may be used. In one example, vanillin turned yellow upon exposure to a threshold limiting level of monomethylhydrazine in five to ten minutes.

These and other objects of the present invention will in part be obvious and will in part appear hereinafter.

The invention accordingly comprises the methods and devices, together with their steps, parts, elements and interrelationships that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

The invention described herein provides a method and apparatus for real-time colorimetric detection of hydrazine and its derivatives by use of benzaldehydes or aromatic conjugated aldehydes with activation in the para position by a substituent —, OH, —NR$_2$, or —OR group. Also, cinnamaldehyde and its substituted derivatives have been found to be effective in the detection of hydrazine and its derivatives.

Various benzaldehyde derivatives are dissolved in suitable solvents, such as diethyl ether, acetone, alcohol or isopropanol to form a solution which when coated on a substrate can be used for the passive, real-time detection of hydrazine and its derivatives. If the coated substrate is used for detecting hydrazine, the pH must be approximately 5 or less and for unsymmetrical dimethylhydrazine, the pH must be adjusted to approximately 2. The solution can be used as a collection media in impinger sampling of low levels of hydrazine in air. Such solutions have detected the presence of hydrazine and its derivatives when used as a coating on substrates such as silica gel. Other substrates, for example, filter paper, silica gel thin layer chromatography plates, silica gel packing and a solid support resin such as sold under the trademark Amberlite IRC-50 (H) resin and microporous membranes have been used as substrates.

One purpose of the invention is to provide an aldehyde-hydrazine condensation reaction which results in a highly colored product that is not pH dependent to a great extent. The aldehyde selected contains a chromophore in order to obtain a visible reaction product.

Figure 1:
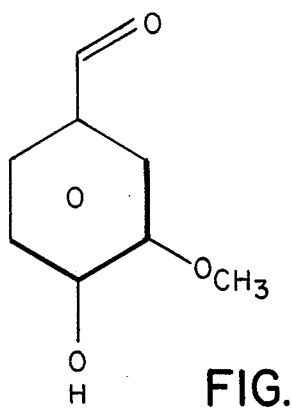
FIG. 1 is a structural formula of vanillin which is used for the detection of hydrazine according to the present invention.

In one example, vanillin, 3-methoxy 4-hydroxyl benzaldehyde, FIG. 1, a non-toxic chemical, was used as a coating on a silica gel substrate that reacted with a monomethylhydrazine (MMH) contaminated gas stream. The coating reacted with the contaminated gas stream and yielded a product that absorbed in the visible region. At threshold limiting value (TLV) exposure, 200 parts-per-billion, the first distinct indication of color came after five to ten minutes when a yellow cast was observed. The yellow color continued to intensify and, after approximately two hours of exposure, it was a very bright lemon yellow. The color development has shown to be linear to approximately 3.8 parts-per-million Hrs which is equivalent to 19 hrs of TVL MMH exposure.

Other benzaldehyde derivatives have been tested and found to provide passive, real-time colorimetric indication of exposure to hydrazine and its derivatives. The most successful candidates are characterized by para-substituents of —OH, —OR, or —NR$_2$. Vanillin has a para-hydroxyl substituent. In the compounds discussed, R has been a methyl group. However, the reaction mechanism should not limit the potential candidates to this substitution. Each of these substituents are known as ortho, para activating groups of benzene. It is believed that other benzaldehyde derivatives which have substituents activating the aldehyde position would also work.

In addition to vanillin, four other compounds have been successfully tested. P-anisaldehyde reacts with hydrazine to form a bright greenish yellow and p-dimethylamino benzaldehyde reacts with hydrazine to form a bright orange. 2,4 - Dimethoxybenzaldehyde and 2,4 - Dihydroxybenzaldehyde provide a yellow indication upon reaction. Typically, the concentration of vanillin, P-anisaldehyde and P-dimethylamino benzaldehyde is in the range of 0.004 grams per milliliter to 0.04 grams per milliliter, preferably 0.007 grams per milliliter. These compounds have been used as coatings on silica gel thin layer chomatography plates. The compounds with a hydroxy group react to MMH without addition of an acid. For reaction with hydrazine and unsymmetrical dimethyihydrazine, the addition of a stronger acid is necessary.

This benzaldehyde class of chemical compounds provides a variety of possibilities in the detection of hydrazines. Analysis of the color change may be determined qualitatively, and in real-time by visualization. Quantitative analysis in real-time is possible by spectroscopic methods. The benzaldehyde compounds may be used in solution, or as coatings on selected sorbents, which opens applications in passive dosimetry, paper tape instruments, detector tubes, liquid impinger sampling, wet chemical analysis, or optical waveguide detection.

Figure 2:
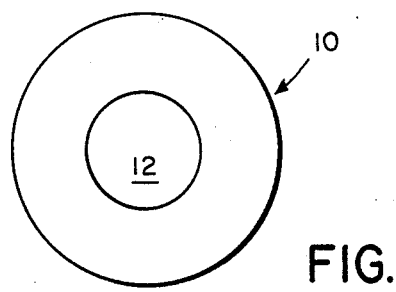
FIG. 2 is a plan view of a passive colorimetric badge embodying the invention.
Figure 3:
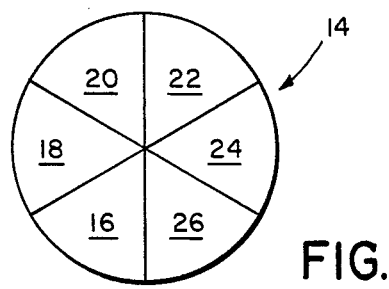
FIG. 3 is a plan view of a color wheel which is used for interpolation of badge color.

FIG. 2 shows a passive colorimetric badge 10, having a substrate 12, that is coated with a benzaldehyde derivative to provide a visual indication of exposure to hydrazine and its derivatives. FIG. 3 shows a color wheel 14 having a plurality of color zones 16, 18, 20, 22, 24 and 26. In the illustrated embodiment, by way of example, color zone 16 has a color which is the equivalent to 0.07 ppm-hours of MMH exposure; color zone 18 has a color which is the equivalent to 0.14 ppm-hours of MMH exposure; color zone 20 has a color which is the equivalent to 0.48 ppm-hours of MMH exposure; color zone 22 has a color which is the equivalent to 1.1 ppm-hours of MMH exposure; color zone 24 has a color which is the equivalent to 3.8 ppm-hours of MMH exposure; and color zone 26 is a standard color of saturation. The badge 10 exposure, i.e., the color of stratum 12, is interpolated from a comparison of badge color with the colors of the zones 16, 18, 20, 22, 24 and 26.

In one example, tests were performed on dilute hydrazone solutions resulting from the reaction of vanillin with MMH. A stock standard of MMH in isopropanol was used to prepare working standards. The vanillin indicator was dissolved in isopropanol and acidified with concentrated hydrochloric acid (HCL). Known amounts of the working standards were added to volumetric flasks containing the vanillin solution. A yellow color developed immediately, indicating formation of the hydrazone.

Vanillin (3-methoxy-4-hydroxybenzeldehyde) has been shown to be an excellent derivatization agent for hydrazine and MMH, through less effective for unsymmetrical dimethylhydrazine UDMH. Due to the chemistry of the reaction, few, if any, interferences are expected. The formation of the hydrazone is a quick and clean reaction. This has been shown in the initial spectrophotometric investigations on dilute MMH standard solutions. Vanillin has not shown extreme pH sensitivity in reacting with MMH, however it is more sensitive to pH in hydrazine and UDMH reactions. This characteristic allows a wider pH range than with, other aldehydes, such as with para-N, N-dimethylaminobenzaldehyde (PDAB) when monitoring MMH.

The vanillin must be in an acidified state to form a visual product upon reaction with hydrazine and UDMH. Results from initial tests, performed using HC1 for the acidification, exhibited detection limits of <0.1 and 0.06 ppm hours for hydrazine and UDMH, respectively. The volatility of HC1 is a source of potential problems, therefore the use of citric, phosphoric and sulphuric acids have been investigated and found to perform successfully for hydrazine.

Vanillin has been investigated as a coating on various substrates with design applications as detector tubes and passive dosimeters. The coating solution can be prepared by dissolving vanillin in acetone and alcohols, it is not water soluble.

For use as a substrate in a passive system, the silica gel glass TLC plates exhibited many desirable qualities. The samples made using TLC plates were affected the least by the relative humidity and in general the color that formed was brighter than with other substrates.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A method for real-time colorimetric detection of hydrazine and its derivatives comprising the step of exposing vanillin to hydrazine, said vanillin providing a colorimetric indication of the presence of hydrazine and its derivatives.

2. A method for real-time colorimetric detection of hydrazine and its derivatives comprising the step of exposing p-anisaldehyde to hydrazine, said p-anisaldehyde providing a colorimetric indicating of the presence of hydrazine and its derivatives.

3. A method for real-time colorimetric detection of hydrazine and its derivatives comprising the step of exposing 2,4-dimethoxybenzaldehyde to hydrazine, said 2,4-dimethoxybenzaldehyde providing a colorimetric indication of the presence of hydrazine and its derivatives.

4. A method for real-time colorimetric detection of hydrazine and its derivatives comprising the step of exposing 2,4-dihydroxybenzaldehyde to hydrazine, said 2,4-dihydroxybenzaldehyde providing a colorimetric indication of the presence of hydrazine and its derivatives.

5. A method for real-time colorimetric detection of hydrazine and its derivatives comprising the steps of:
   (a) providing a substrate coated with vanillin; and
   (b) exposing said coated substrate to hydrazine, said vanillin coating providing a colorimetric indication of the presence of hydrazine and its derivatives.

6. A method for real-time colorimetric detection of hydrazine and its derivatives comprising the steps of:
   (a) providing a substrate coated with P-anisaldehyde; and
   (b) exposing said coated substrate to hydrazine, said P-anisaldehyde coating providing a colorimetric indicating of the presence of hydrazine and its derivatives.

7. A method for real-time colorimetric detection of hydrazine and its derivatives comprising the steps of:
   (a) providing a substrate coated with 2,4-dimethoxybenzaldehyde; and
   (b) exposing said coated substrate to hydrazine, said 2,4-dimethoxybenzaldehyde coating providing a colorimetric indication of the presence of hydrazine and its derivatives.

8. A method for real-time colorimetric detection of hydrazine and its derivatives comprising the steps of:
   (a) providing a substrate coated with 2,4-dihydroxybenzaldehyde; and
   (b) exposing said coated substrate to hydrazine, said 2,4-dihydroxybenzaldehyde coating providing a colorimetric indicating of the presence of hydrazine and its derivatives.

9. A method for real-time colorimetric detection of hydrazine and its derivatives comprising the steps of:
   (a) providing a substrate coated with a solution containing vanillin at a concentration in the range of 0.004 grams per milliliter to 0.04 grams per milliliter; and
   (b) exposing the coated substrate to hydrazine, the vanillin providing a colorimetric indication of the presence of hydrazine and its derivatives.

10. The method as claimed in claim 9 wherein said substrate is a silica gel substrate.

11. The method as claimed in claim 9 wherein said substrate is paper.

12. The method as claimed in claim 9 wherein said substrate is a microporous membrane.

13. The method as claimed in claim 9 including the step of providing a plurality of color zones adjacent the coated substrate.

14. The method as claimed in claim 13 wherein said color zones have different colors which correspond to different hydrazine exposure levels.

15. The method as claimed in claim 9 including the step of providing a plurality of color zones.

* * * * *

UNITED STATES PATENT AND TRADEMARK OFFICE
CERTIFICATE OF CORRECTION

PATENT NO. : 4,900,681
DATED : February 13, 1990
INVENTOR(S) : Patricia Taffe et al.

It is certified that error appears in the above-identified patent and that said Letters Patent is hereby corrected as shown below:

Claim 2, column 4, line 63, delete "indicating" and insert in its place -- "indication" --;

Claim 6, column 5, line 22, delete "indicating" and insert in its place --"indication" --; and Claim 8, column 6, line 7, delete "indicating" and insert in its place -- "indication" --.

Signed and Sealed this

Nineteenth Day of February, 1991

Attest:

HARRY F. MANBECK, JR.

*Attesting Officer*   *Commissioner of Patents and Trademarks*